US 9,993,300 B2

(12) United States Patent
Inoue

(10) Patent No.: US 9,993,300 B2
(45) Date of Patent: Jun. 12, 2018

(54) MANIPULATOR

(71) Applicant: OLYMPUS CORPORATION, Tokyo (JP)

(72) Inventor: Shintaro Inoue, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 305 days.

(21) Appl. No.: 14/821,313

(22) Filed: Aug. 7, 2015

(65) Prior Publication Data

US 2016/0030121 A1 Feb. 4, 2016

Related U.S. Application Data

(63) Continuation of application No. PCT/JP2014/053235, filed on Feb. 5, 2014.

(60) Provisional application No. 61/762,386, filed on Feb. 8, 2013.

(51) Int. Cl.
*G06F 19/00* (2018.01)
*A61B 19/00* (2006.01)
*A61B 34/00* (2016.01)

(52) U.S. Cl.
CPC .......... *A61B 19/2203* (2013.01); *A61B 34/70* (2016.02); *A61B 34/71* (2016.02); *A61B 34/74* (2016.02)

(58) Field of Classification Search
None
See application file for complete search history.

(56) References Cited

U.S. PATENT DOCUMENTS

| 5,817,119 A | 10/1998 | Klieman et al. |
| 8,409,245 B2 | 4/2013 | Lee |
| 2002/0082612 A1* | 6/2002 | Moll ................. A61B 19/2203 606/130 |
| 2007/0005045 A1* | 1/2007 | Mintz .................... B25J 9/0084 606/1 |
| 2007/0013336 A1* | 1/2007 | Nowlin .................. B25J 9/1682 318/568.21 |
| 2009/0112230 A1 | 4/2009 | Jinno |

(Continued)

FOREIGN PATENT DOCUMENTS

| CN | 101677814 A | 3/2010 |
| CN | 101732093 A | 6/2010 |

(Continued)

OTHER PUBLICATIONS

Extended Supplementary European Search Report dated Sep. 23, 2016 received in PCT/JP2014053235.

(Continued)

*Primary Examiner* — Bhavesh V Amin
(74) *Attorney, Agent, or Firm* — Scully, Scott, Murphy & Presser, P.C.

(57) ABSTRACT

The invention provides an easy-to-manipulate manipulator comprising a manipulating part, a manual joint part that is driven directly by displacement of the manipulating part, a detection unit for detecting an amount of displacement of the manipulating part, a device that moves depending on the amount of displacement detected at the detection unit, an electric joint part that is driven by the device, and a selection portion for selectively determining whether the electric joint part is driven or not.

7 Claims, 12 Drawing Sheets

(56) References Cited

U.S. PATENT DOCUMENTS

| | | | |
|---|---|---|---|
| 2010/0280525 A1* | 11/2010 | Alvarez | A61B 17/00234 606/130 |
| 2012/0215220 A1* | 8/2012 | Manzo | A61B 18/1445 606/46 |
| 2012/0310221 A1* | 12/2012 | Durant | A61B 34/71 606/1 |
| 2012/0316573 A1* | 12/2012 | Durant | A61B 19/2203 606/130 |
| 2013/0046318 A1* | 2/2013 | Radgowski | A61B 34/30 606/130 |

FOREIGN PATENT DOCUMENTS

| | | |
|---|---|---|
| EP | 2 548 529 A1 | 1/2013 |
| JP | 2005-524442 A | 8/2005 |
| JP | 2005211682 A | 8/2005 |
| JP | 2009107087 A | 5/2009 |
| JP | 2010253162 A | 11/2010 |
| JP | 2010253205 A | 11/2010 |
| WO | 03/092523 A1 | 11/2003 |

OTHER PUBLICATIONS

International Search Report dated May 20, 2014 received in International Application No. PCT/JP2014/053235.

* cited by examiner

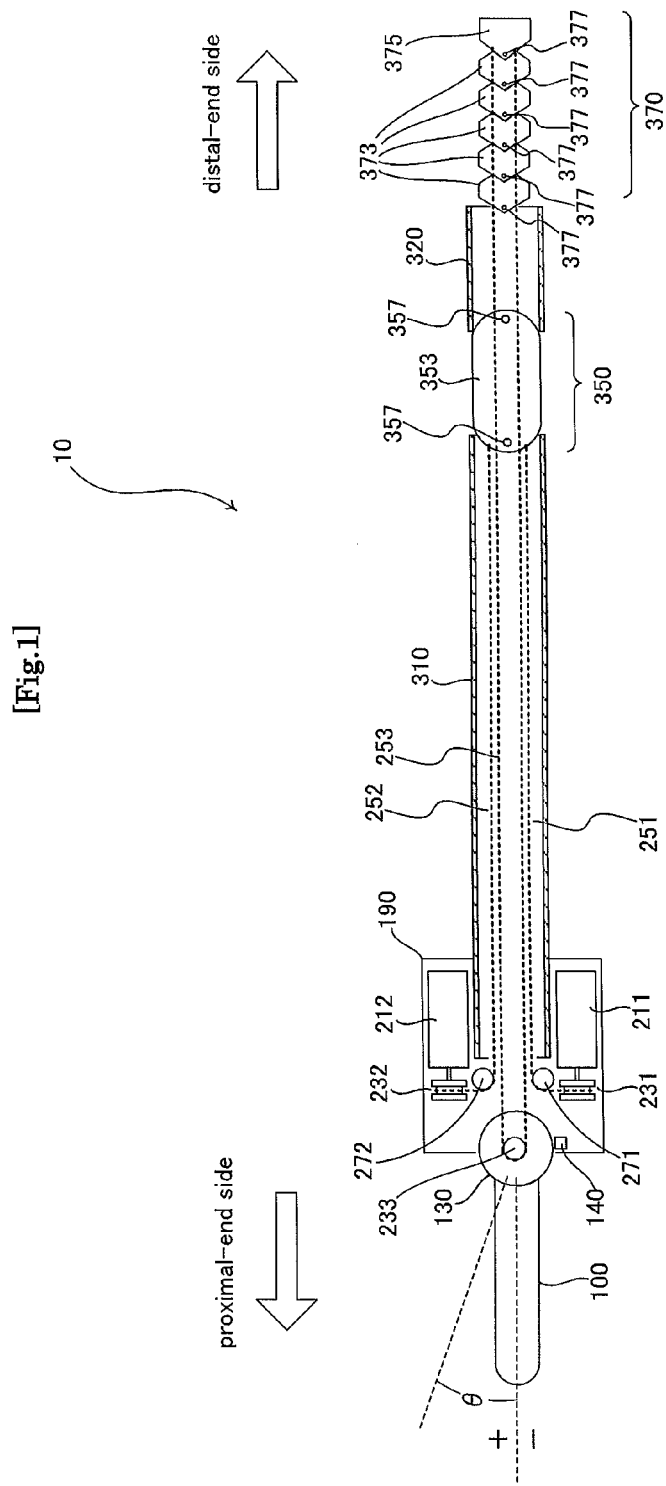

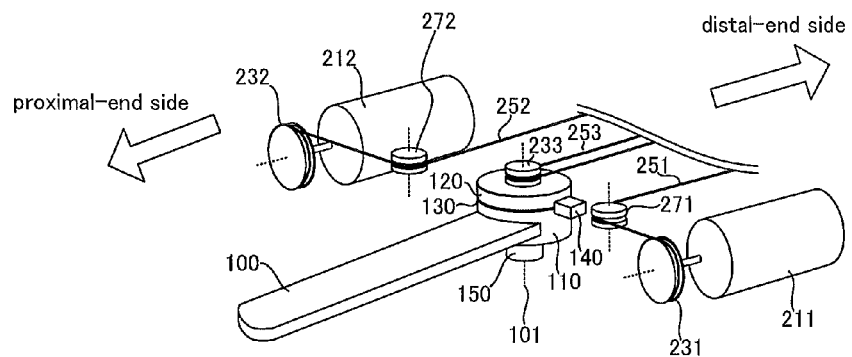
[Fig. 2]
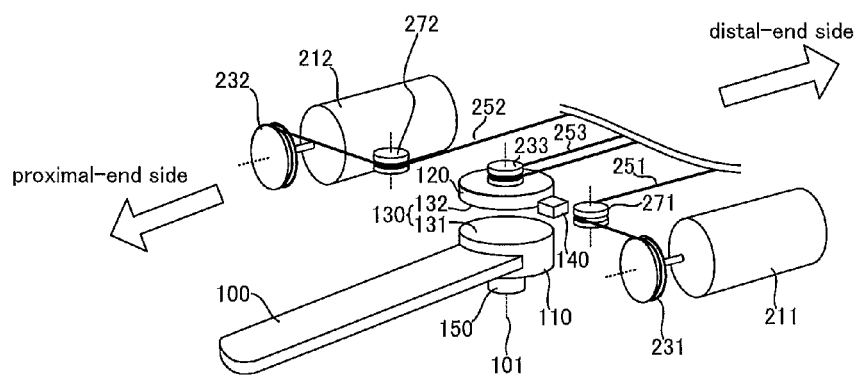
[Fig. 3]

[Fig.4]
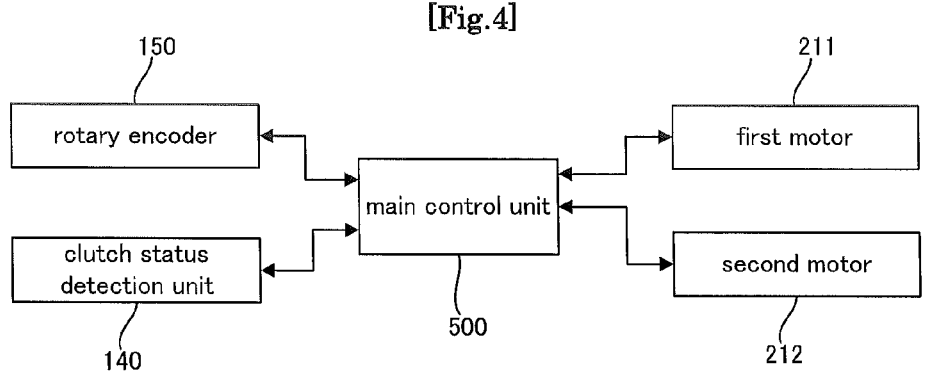
[Fig.5]
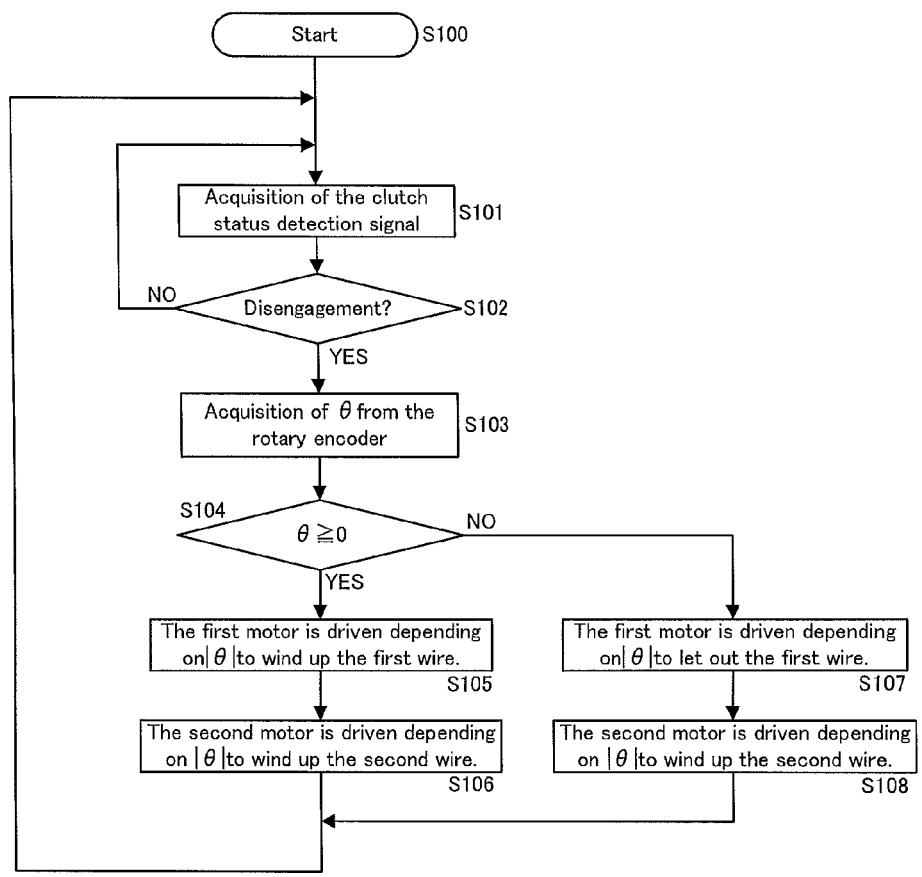

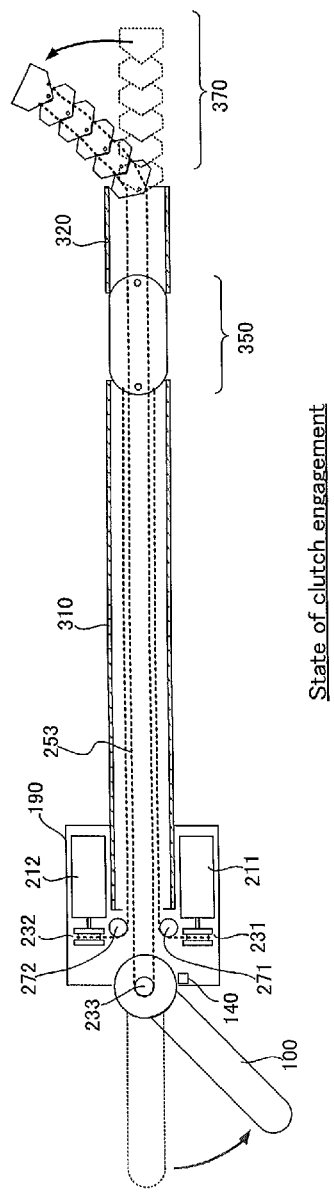
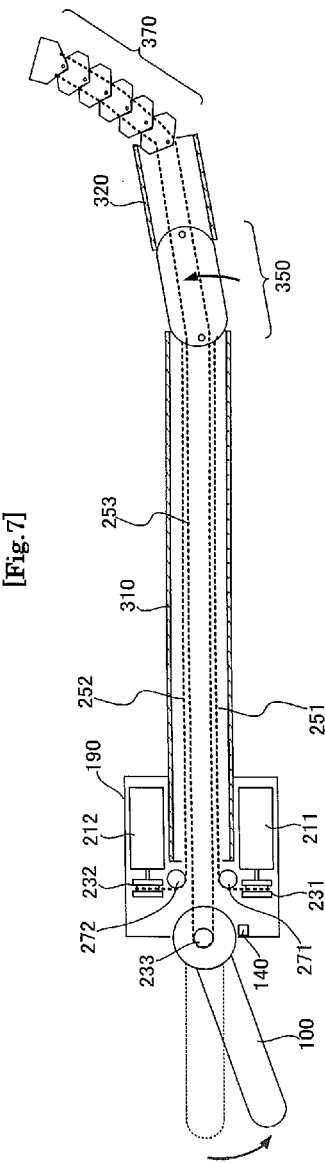

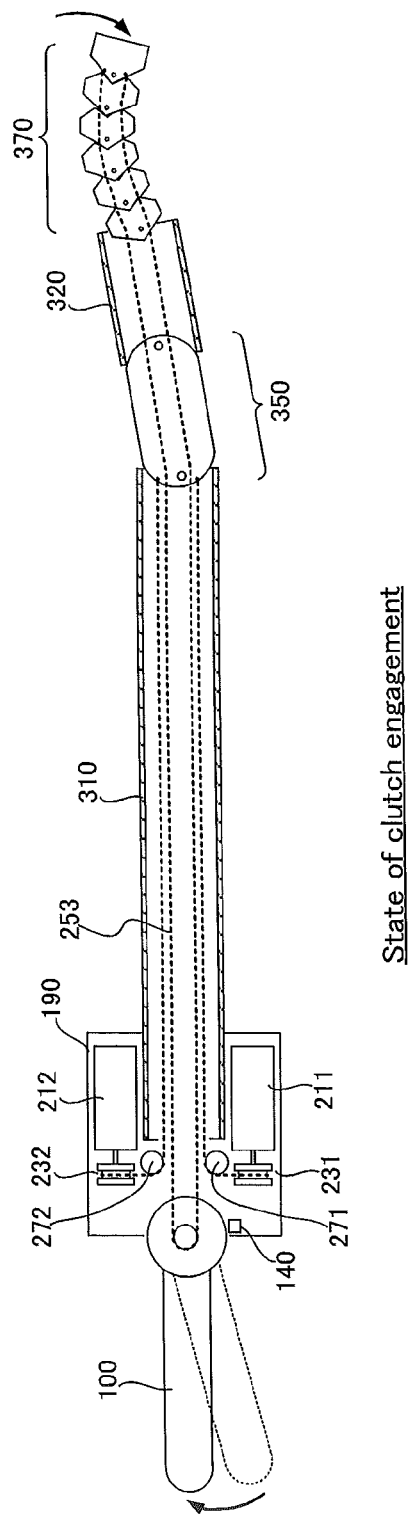
[Fig.8]
State of clutch engagement

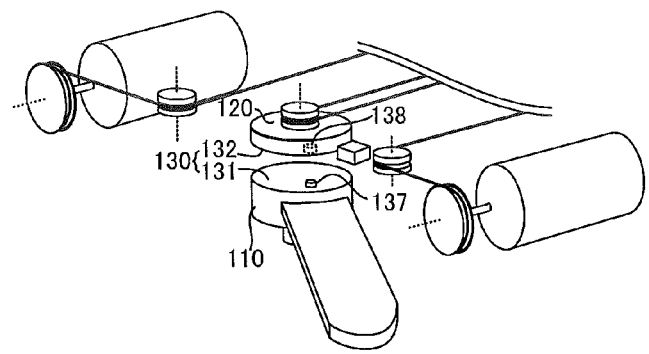
[Fig. 9]
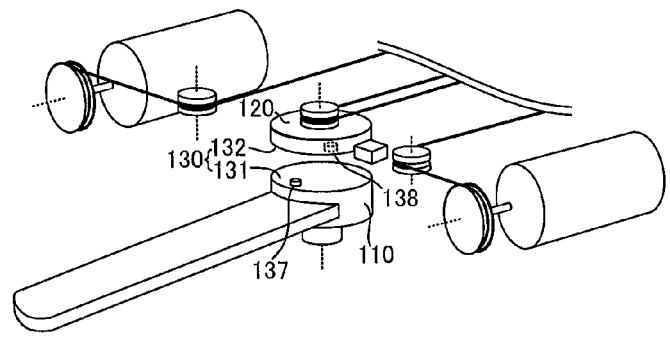
[Fig. 10]
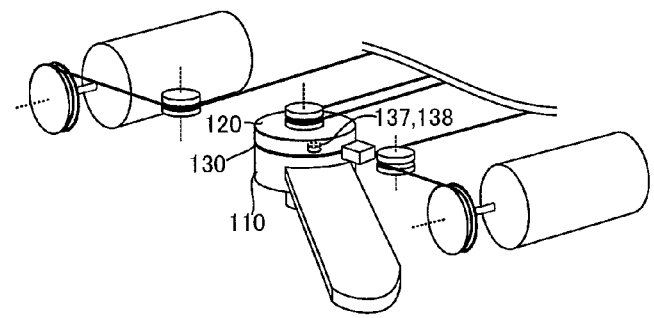
[Fig. 11]

[Fig.12]
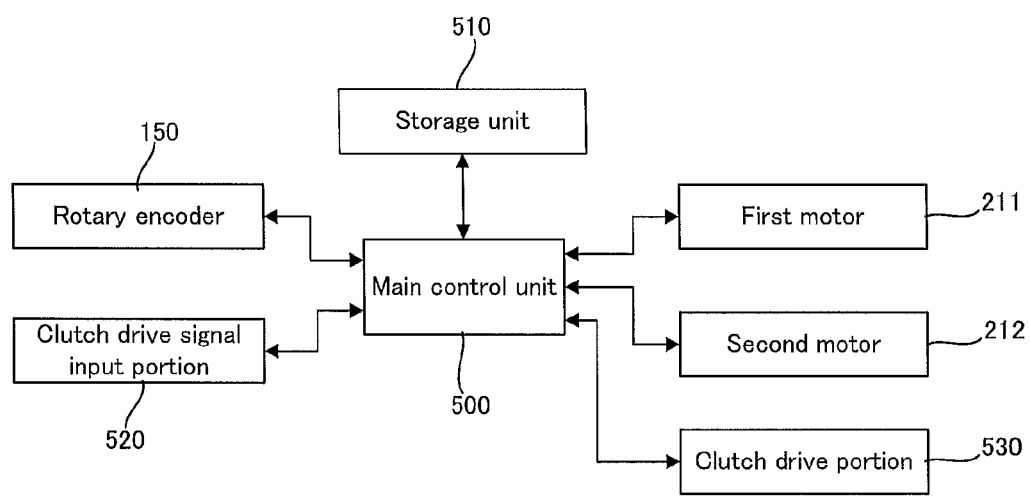

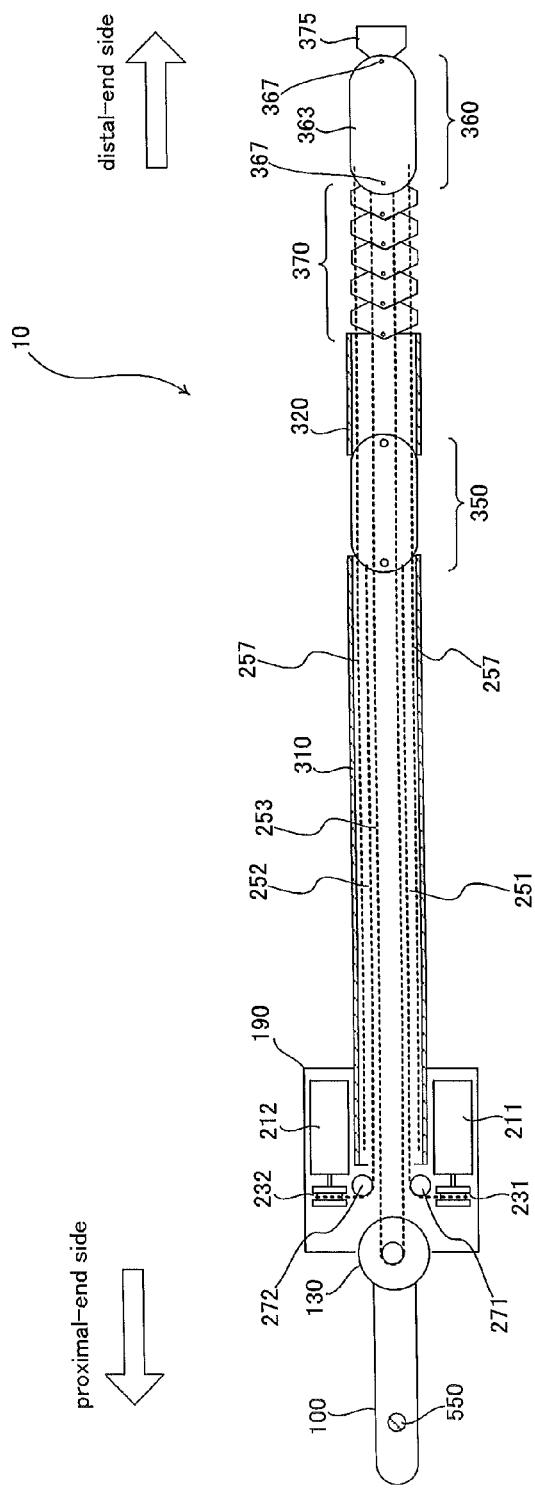
[Fig.13]

[Fig.14]
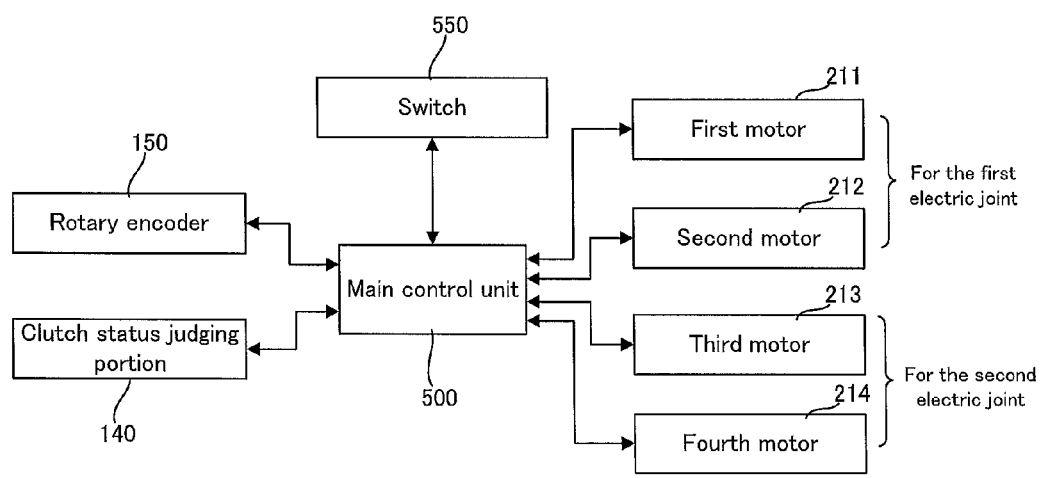

[Fig.15]
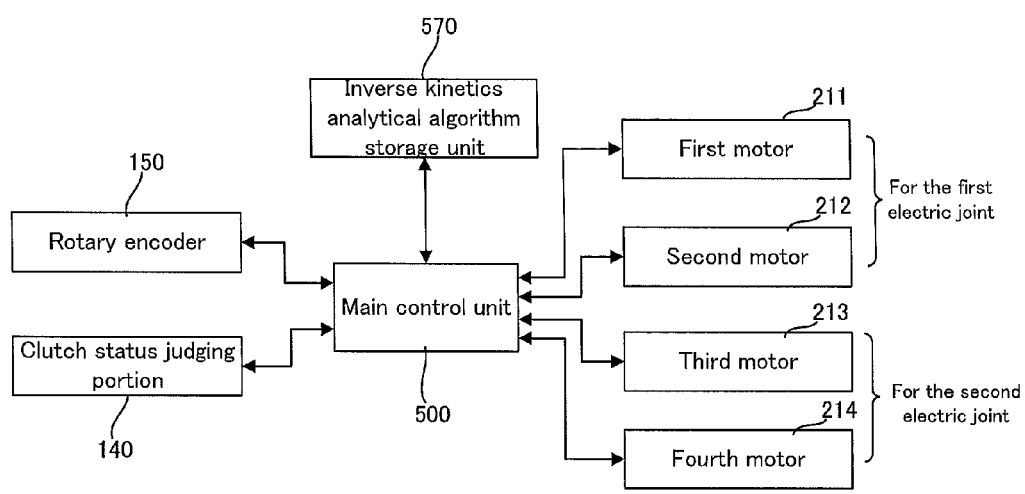

[Fig.16]
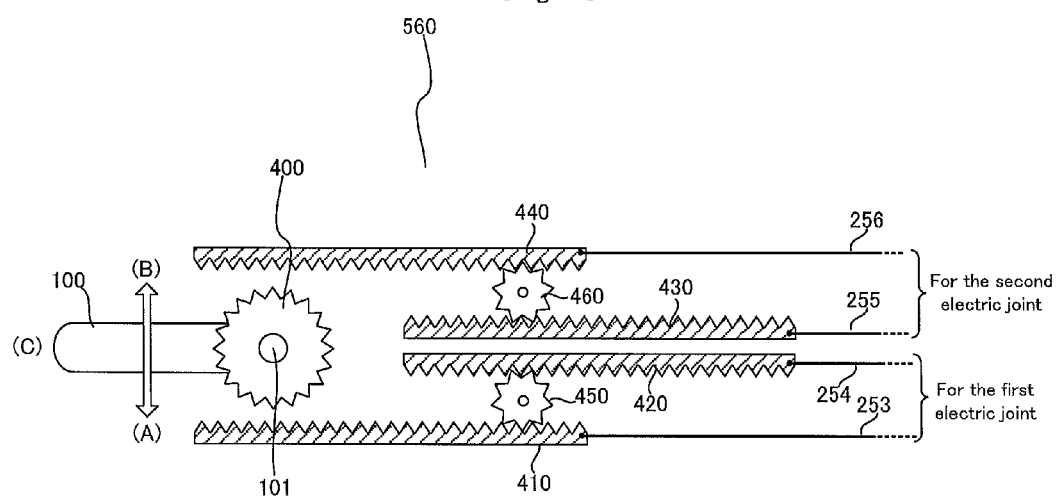
[Fig.17]
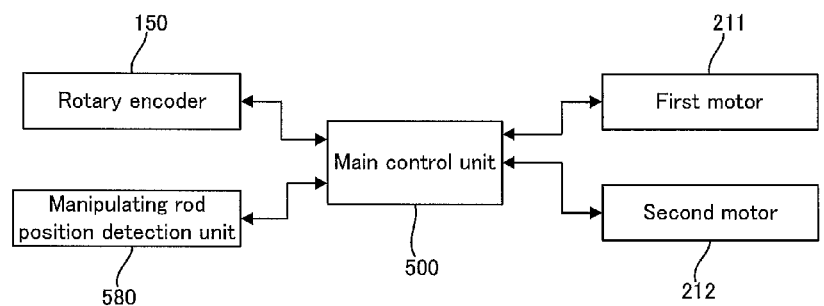

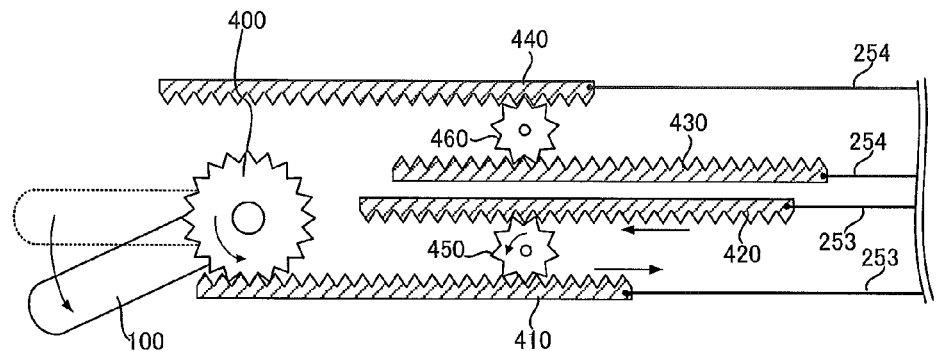
[Fig. 18]
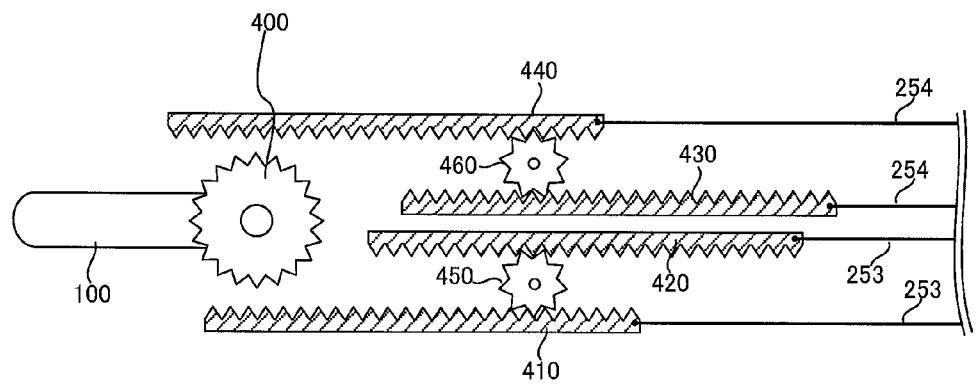
[Fig. 19]
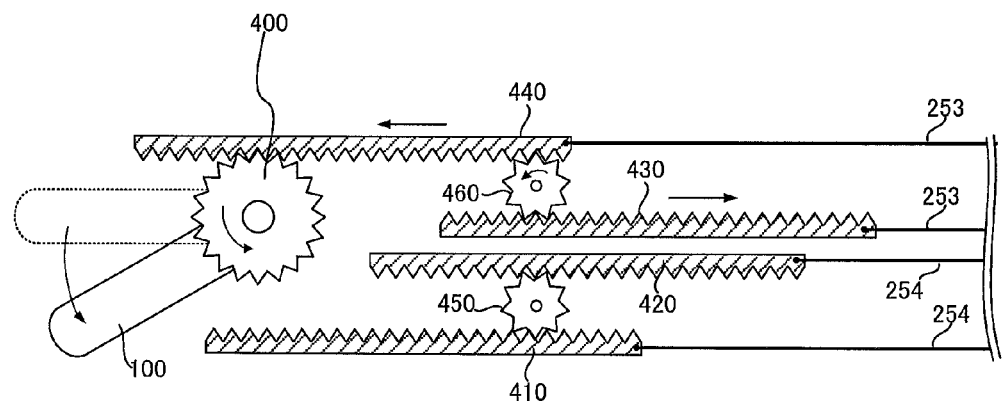
[Fig. 20]

MANIPULATOR

CROSS-REFERENCES TO RELATED APPLICATIONS

This application is a Continuation Application of International Application PCT/JP2014/053235 filed on Feb. 5, 2014, which claims priority to U.S. Application No. 61/762,386 filed on Feb. 8, 2013. The Contents of International Application PCT/JP2014/053235 and U.S. Patent application No. 61/762,386 are hereby incorporated by reference herein in its entirety.

BACKGROUND OF THE INVENTION AND RELATED ART STATEMENT

The present invention relates generally to a medical manipulator that is inserted into the body cavity and used for applying treatments to various tissues in it.

So far there has been a medical manipulator system known as an operation support system, the manipulator system comprising a master manipulator manipulated by an operator and a slave manipulator adapted to implement treatment based on manipulation of the master manipulation.

In surgical operation using such a medical manipulator system, an endoscope, a manipulator (or forceps) or the like are inserted into the abdomen or the like of a patient through some small holes so that the operator can implement operation while viewing images from the endoscope through a monitor. Such laparoscopic surgery is now expected to be applicable to a wider range of fields, because it is less invasive due to no need for opening up the abdomen, and because of some considerable reductions in the number of days taken by the time of post-operative recuperation and until the patient is discharged out of hospital.

For instance, Patent Publication 1 (JP(A) 2010-253162) discloses such a system comprising a manually manipulated joystick, a robot arm that is electrically driven in association with movement of the joystick, a trigger lever that is formed integrally with the joystick and manually manipulated to advance or retract a first wire, and a manipulator mounted to the tip of the robot arm.

SUMMARY OF THE INVENTION

The present invention provides a manipulator, comprising:
a manipulating part,
a manual joint portion that is driven directly by displacement of the manipulating part,
a detection unit that detects an amount of displacement of the manipulating part,
a device that moves depending on the amount of displacement detected at the detection unit,
an electric joint portion that is driven by the device, and
a selection portion that selectively determines whether the electric joint portion is driven or not.

Preferably, in the manipulator of the invention, the selection portion is a clutch.

Preferably, in the manipulator of the invention, when driving of the manual joint portion is selected at the selection portion, the clutch is engaged to transmit the displacement of the manipulating part to the manual joint portion.

Preferably, in the manipulator of the invention, when driving of the electric joint portion is selected at the selection portion, the clutch is disengaged to move the device depending on the amount of displacement detected at the detection unit.

Preferably, in the manipulator of the invention further comprises a disengagement position status holding portion for holding a position status between clutch plates upon disengagement of the clutch.

Preferably, in the manipulator of the invention, the disengagement position status holding portion comprises a convex portion provided on one clutch plate and a concave portion provided in another clutch plate.

Preferably, in the manipulator of the invention, the disengagement position status holding portion is a storage portion for electromagnetically storing the amount of displacement detected at the detection unit upon disengagement of the clutch.

Preferably, in the manipulator of the invention further comprises:
a plurality of the electric joint portions, and an electric joint portion selection switch for selecting which of the plurality of the electric joint portions is to be driven.

Preferably, in the manipulator of the invention further comprises:
a plurality of the electric joint portions,
a plurality of the devices corresponding to the plurality of the electric joint parts, respectively, and
a control unit for implementing operation based on the amount of displacement detected at the detection unit to issue commands to the plurality of the devices about how much each of the plurality of the devices is driven.

Preferably, in the manipulator of the invention, the operation is an operation for solving inverse kinetics.

Preferably, in the manipulator of the invention further comprises:
a plurality of the manual joint portions, and
a manual joint portion selection switch for selecting which of the plurality of the manual joint portions is to be driven.

The present invention also provides a manipulator, comprising:
a manipulating part,
a plurality of manual joint portions that are driven directly by displacement of the manipulating part,
a detection unit for detecting an amount of displacement of the manipulating part,
a device that moves depending on the amount of displacement detected at the detection unit,
an electric joint portion that is driven by the device, and
a selection portion for selectively determining whether the plurality of the manual joint parts are driven or the electric joint part is driven.

Preferably, in the manipulator of the invention, the selection portion comprises a rack-and-pinion mechanism.

BRIEF DESCRIPTION OF DRAWINGS

FIG. 1 is schematically illustrative of the architecture of the manipulator 10 according to one embodiment of the invention.

FIG. 2 is a perspective view of the internal architecture of the base case 190 upon engagement of the clutch 130.

FIG. 3 is a perspective view of the internal architecture of the base case 190 upon disengagement of the clutch 130.

FIG. 4 is a block diagram of the manipulator 10 according to one embodiment of the invention.

FIG. 5 is a flowchart of a control flow of the manipulator 10 according to one embodiment of the invention.

FIG. 6 is illustrative of an exemplary manipulation of the manual joint portion 370 of the manipulator 10 according to one embodiment of the invention.

FIG. 7 is illustrative of an exemplary manipulation of the electric joint portion 350 of the manipulator 10 according to one embodiment of the invention.

FIG. 8 is illustrative of an exemplary manipulation of the manual joint portion 370 of the manipulator 10 according to one embodiment of the invention.

FIG. 9 is illustrative of the architecture of an essential part of the manipulator 10 according to another embodiment of the invention.

FIG. 10 is illustrative of the architecture of an essential part of the manipulator 10 according to yet another embodiment of the invention.

FIG. 11 is illustrative of the architecture of an essential part of the manipulator 10 according to a further embodiment of the invention.

FIG. 12 is a block diagram of the manipulator 10 according to a further embodiment of the invention.

FIG. 13 is schematically illustrative of the architecture of the manipulator 10 according to a further embodiment of the invention.

FIG. 14 is a block diagram of the manipulator 10 according to a further embodiment of the invention.

FIG. 15 is a block diagram of the manipulator 10 according to a further embodiment of the invention.

FIG. 16 is illustrative of an example of the construction of the manual joint selection switch 560 using a rack-and-pinion mechanism.

FIG. 17 is a block diagram of the manipulator 10 according to a further embodiment of the invention.

FIG. 18 is illustrative of an exemplary manipulation of the manual joint portion 370 of the manipulator 10 according to a further embodiment of the invention.

FIG. 19 is illustrative of an exemplary manipulation of the electric joint portion 350 of the manipulator 10 according to a further embodiment of the invention.

FIG. 20 is illustrative of an exemplary manipulation of the manual joint portion 370 of the manipulator 10 according to a further embodiment of the invention.

DETAILED DESCRIPTION OF THE PREFERRED EMBODIMENTS

Some embodiments of the invention are now explained with references to the accompanying drawings. FIG. 1 is schematically illustrative of the architecture of the manipulator 10 according to an embodiment of the invention; FIG. 2 is a perspective view of the internal architecture of the base case 190 upon engagement of the clutch 130; FIG. 3 is a perspective view of the internal architecture of the proximal case 190 upon disengagement of the clutch 130; and FIG. 4 is a block diagram of the manipulator 10 according to one embodiment of the invention. Note here that in FIGS. 2 and 3, dotted lines are indicative of the shafts of rotation of pulleys or the like.

It is to be understood that the embodiment of the invention here is nothing less than one exemplary architecture for reducing the invention down to practice. By way of illustration but not by way of limitation, the following embodiment is explained with reference to the use of a motor as the device for driving the electric joint portion 350. For instance, use may also be made of an actuator such as a solenoid utilizing electric energy, and an actuator such as a pneumatic cylinder employing energies other than electric energy.

In FIG. 1, the left and right sides are indicative of the proximal and distal end sides, respectively. In use, the manipulator 10 is inserted at the distal end side into the body cavity of a patient. It is here presumed that the manipulator 10 includes an end effector (not shown) inserted from the proximal end side to the distal end side to view and treat the patient's body cavity. Although the manipulator 10 here is explained with reference to a type where a treatment tool having an end effector is inserted in place, it is to be noted that the present invention may be extended to an assembly wherein the end effector is integral with the manipulator 10 per se in a non-detachable manner.

A base case 19 positioned on the distal end side includes a manipulating rod 100 manipulated by an operator of the manipulator 10. This manipulating rod 100 may be displaced by a given angle with 101 as the center of rotation.

For example and without limitation, the embodiment of the invention here is explained with reference to the use of the manipulating rod 100 as the manipulating part of the manipulator 10; however, other input devices such as a rotating knob may optionally be used.

In the embodiment of the invention here, the manipulating rod 100 is described as being capable of manipulation only in a two-dimensional plane, and an electric joint portion 350 and a manual joint portion 370 are described typically as being driven in the two-dimensional plane; however, the invention may also be extended to where the manipulating rod 100 capable of manipulation in a three-dimensional space is used to drive the electric and manual joint portions 350 and 370 in the three-dimensional space.

The manipulating rod 100 is formed integrally with a first rotating base portion 110 that is provided with a first clutch plate 131 forming one part of a clutch 130. A second rotating base portion 120 is provided with a second clutch plate 132 forming another part of the clutch 130.

The first and second clutch plates 131 and 132 come in contact with each other to engage the clutch 130 so that the first and second rotating base portions 110 and 120 are linked and operate together. Consequently, the amount of displacement based on the manipulation of the manipulating rod 100 is transmitted to the second rotating base portion 120.

As the first clutch plate 131 is spaced away from the second clutch plate 132 to disengage the clutch 130, it prevents the amount of displacement based on the manipulation of the manipulating rod 100 from transmission to the second rotating base portion 120 side.

Whether the clutch 130 is engaged or disengaged is manually implemented through a mechanism (not shown). Near the clutch 130 there is a clutch status detection unit 140 provided to detect whether the clutch 130 is engaged or disengaged. For this clutch status detection unit 140 there may a mechanical or optical sensor employed.

While the embodiment of the invention here is described typically with reference to manual selection of the engagement or disengagement of the clutch 130, it is to be understood that the engagement or disengagement of the clutch 130 may be electrically selected. A generally available clutch such as a claw clutch or an electromagnetic clutch may be used for that clutch 130.

A detection signal for the status of the clutch 130 detected at the clutch status detection unit 140 is sent out to a main control unit 500. For example, a general-purpose microcomputer may be used for this main control unit 500 whose function may be achieved by having a program run by the aforesaid microcomputer.

A rotary encoder 150 is operable to detect to what degree the first rotating base portion 110 rotates with 101 as the center of rotation. Specifically, the rotary encoder 150 provides a detection part for detecting the amount of displacement of the manipulating rod 100. A detection signal from this rotary encoder 150 is sent out to the main control unit 500.

In the embodiment of the invention here, an angle θ of the first rotating base portion 110 acquired by the rotary encoder 150 is used as the amount of displacement of the manipulating rod 100. If the manipulating rod 100 is of a sliding type and the manipulation of that manipulating rod 100 is acquired by a linear encoder or the like, on the other hand, the amount of displacement of the manipulating rod 100 may then be obtained in the form of distance information.

In the embodiment of the invention here, a positive angle of rotation θ at the time when the manipulating rod 100 takes a position above the horizontal in FIG. 1, and a negative angle of rotation θ at the time when the manipulating rod 100 takes a position below the horizontal in FIG. 1 are detected by the rotary encoder 150.

The main control unit 500 sends a control command signal to a first motor 211 and a second motor 212 that are devices for driving the electric joint portion 350 so that the motion of the electric joint portion 350 can be controlled.

From the base case 190, a first rigid tube 310, electric joint portion 350, second rigid tube 320 and manual joint portion 370 extend in order toward the distal end side. The first and second rigid tubes 310 and 320 are relatively rigid and less likely to bend. Instead of the first and second rigid tubes 310 and 320, however, it is also possible to use flexible tubes that are relatively flexible and capable of bending elastically.

The electric joint portion 350 located between the first and second rigid tubes 310 and 320 includes a cylindrical ring 353, a plurality of rivet-form shaft members 357, a first wire 251 and a second wire 252. The rivet-form shaft members 357 link the joint ring 353 together in a bendable way to form a joint.

The first wire 251 is fixed at one end to the joint ring 353 by brazing or the like, and at the other end to a first drive pulley 231. The first wire 251 is further wound on a first follower pulley 271. The first drive pulley 231 is mounted to the rotary shaft of the first motor 211 to wind up and let out the first wire 251 as the first motor 211 is rotated and driven, whereby the rotational driving force of the first motor 211 is transmitted to the joint ring 353.

The second wire 252 is fixed at one end to the joint ring 353 by brazing or the like, and at the other end to a second drive pulley 232. The second wire 252 is further wound on a second follower pulley 272. The second drive pulley 232 is mounted to the rotary shaft of the second motor 212 to wind up and let out the second wire 252 as the second motor 212 is rotated and driven, whereby the rotational driving force of the second motor 212 is transmitted to the joint ring 353.

The embodiment of the invention here is described typically with reference to the driving of the electric joint portion 350 using two motors: the first motor 211 and the second motor 212; however, the electric joint portion 350 may be driven by a single motor.

When the clutch 130 is disengaged, an angle of rotation θ of the first rotating base portion 110 in association with manipulation of the manipulating rod 100 is acquired by the rotary encoder 150. The angle of rotation θ acquired by the rotary encoder 150 is entered in the main control unit 500. The main control unit 500 controls the first and second motors 211 and 212 depending on the angle θ. This enables the operator to move the electric joint portion 350 on the basis of manipulation of the manipulating rod 100. Upon manipulation of the electric joint portion 350, the operator cannot perceive external forces at the distal-end joint ring 375, etc.

The manual joint portion 370 extending from the second rigid tube 320 toward the distal end includes a plurality of cylindrical joint rings 373, a plurality of rivet-form shaft members 377 and a third wire 253. The rivet-form shaft members 377 link the respective joint rings 373 together in a bendable way to form a joint. The third wire 253 is fixed at both its ends to the distal-end joint ring 375 by brazing or the like, and wound on a third drive pulley 233. The third drive pulley 233 is fixed to the second rotating base portion 120 to rotate as the second rotating base portion 120 rotates with 101 as the center of rotation.

With the clutch 130 engaged, the first and second rotating base portions 110 and 120 are so linked together that the third drive pulley 233 rotates by manipulation of the manipulating rod 100, whereby the manipulation by the operator of the manipulating rod 100 is transmitted to the manual joint portion 370. Such manipulation of the manual joint portion 370 makes it possible for the operator to perceive external forces at the distal end joint ring 375, etc.

How the manipulator 10 set up according to the embodiment of the invention here is controlled will then be explained with reference to FIG. 5 that is a flowchart illustrative of a control flow run by the manipulator 10 according to the embodiment of the invention here. Such a flowchart is run by the main control unit 500.

Referring to FIG. 5, the control flow is started in Step S100, and a detection signal from the clutch status detection unit 140 is acquired in the following Step S101. In Step S102, whether the clutch 130 is disengaged or not is judged on the basis of the detection signal from the clutch status detection unit 140.

When the judgment in Step S102 is NO or when the clutch 130 remains engaged, the operator is just about to manipulate the manual joint portion 370. At this time the main control unit 500 does not execute control of the first and second motors 211 and 212 or the like as yet.

When the judgment in Step S102 is YES or the clutch 130 remains disengaged, on the other hand, the control flow goes to Step S103 to acquire the angle θ from the rotary encoder 150.

Subsequently, whether or not θ≥0 is judged in Step S104.

When the judgment in Step S104 is YES, the first motor 211 is driven in Step S105 depending on |θ| to wind up the first wire 251, and the second motor 212 is driven in Step S106 depending on |θ| to let out the second wire 252.

When the judgment in Step S104 is NO, on the other hand, the first motor 211 is driven in Step S107 depending on |θ| to let out the first wire 251, and the second motor 212 is driven in Step S108 depending on |θ| to wind up the second wire 252.

A specific example of manipulation of the manipulator 10 according to the embodiment of the invention here based on such control as described above will now be explained with reference to FIGS. 6, 7 and 8 showing such an example.

As the operator keeps the clutch 130 engaged, it causes the manual joint portion 370 to move by manipulation of the manipulating rod 100, as shown in FIG. 7. At this time the manual joint portion 370 is being driven directly by displacement of the manipulating rod 100 so that the operator can perceive external forces at the distal end joint ring 375, etc.

Subsequently, as the operator keeps the clutch 130 disengaged, it causes the electric joint portion 350 to move by manipulation of the manipulating rod 100, as shown in FIG. 6. While the first and second motors 211 and 212 are controlled on the basis of the information acquired at the rotary encoder 150, the electric joint portion 350 moves; in this state the operator cannot perceive external forces at the distal end joint ring 375, etc.

FIG. 8 illustrates that the operator again engages the clutch 130, allowing the manual joint portion 370 to move by manipulation of the manipulating rod 100.

The manipulator 10 according to such an embodiment as described above comprises the manual joint portion 370 capable of being driven directly by displacement of the manipulating rod 370 to perceive an external force at a distal-end motion portion and the electric joint portion 350 that is driven by a device moving on electric energy but is incapable of perceiving an external force at the distal-end motion portion so that both the joint portions can be selected at the selection portion and manipulated at the single manipulating rod 100 such as the clutch 130, making it easy for an operator to implement manipulations.

In what follows, another and further embodiments of the invention will be explained. In the embodiment of the invention so far explained herein, the manual joint portion 370 is moved by manipulation of the manipulating rod 100 to disengage the clutch 130 once for manipulation of the electric joint portion 350, after which the clutch 130 is again engaged to manipulate the manual joint portion 370. In this case, there is a problem in that the relations between the last angles of the manual joint portion 370 and manipulating rod 100 are not restored back.

According to the embodiment of the invention described here, that problem can be overcome by keeping the position status between the clutch plates intact upon disengagement of the clutch 130.

Keeping the position status between the clutch plates intact may be achieved by physical means or an electromagnetic storage element. First of all, the former physical means is explained with reference to FIGS. 9 to 11.

To keep the position status between the clutch plates intact upon disengagement of the clutch 130, for instance, the manipulator 10 according to the embodiment of the invention here includes a first clutch plate 131 having a convex portion 137 and another, second clutch plate 132 having a concave portion 138 for receiving that convex portion 137.

In such an arrangement as described above, the manipulating rod 100 is first manipulated to move the manual joint portion 370 to disengage the clutch 130 once. In this case, the position of the second rotating base portion 120 having the second clutch plate 132 is held by the position of the concave portion 138.

When it is intended to manipulate the electric joint portion 350 and then again engage the clutch 130 for manipulation of the manual joint portion 370, the clutch 130 would be not engaged where the manipulating rod 100 is located in such a position as shown typically in FIG. 10.

Then, the operator can adjust the position of the manipulating rod 100 to search for a position where the convex portion 137 of the first clutch plate 131 is fitted into such a concave portion 138 of the second clutch plate 132 as shown in FIG. 11 for engagement of the clutch 130 whereby upon re-engagement of the clutch 130, the status between the last angles of the manual joint portion 370 and manipulating rod 100 can be restored back, making it possible for the operator to implement more intuitive manipulations.

In the embodiment as described above, the convex portion 137 is provided on the first clutch plate 131 and the concave portion 138 is provided in the second clutch plate 132 to physically keep the position status between the clutch plates intact; however, the arrangement provided on the clutch plates for that purpose is not limited to such a concavo-convex arrangement.

In what follows, an example of keeping the position status between the clutch plates intact by means of an electromagnetic storage element will be explained with reference to FIG. 12 that is a block diagram of the manipulator 10 according to yet another embodiment of the invention.

In the embodiments of the invention described so far, whether the clutch 130 is to be engaged or disengaged is manually implemented through the mechanism not shown in the drawings; in the embodiment of the invention here, however, an electromagnetic clutch is used as the clutch 130 so that the clutch 130 can be engaged or disengaged electromagnetically by a clutch drive portion 530.

It is also possible for the operator to selectively engage or disengage the clutch 130 by giving a command to a clutch drive signal input portion 520.

In the embodiment of the invention here, there is a storage unit 510 provided to electromagnetically store the amount of displacement (angle θ in this embodiment) detected at the rotary encoder 150 upon disengagement of the clutch 130. For such a storage unit 510, use may be made of a storage area in the microcomputer or, alternatively, a separate memory.

In such an arrangement as described above, the manual joint portion 370 is first moved by manipulation of the manipulating rod 100 to disengage the clutch 130 once, in which case the angle θ detected at the rotary encoder 150 is stored in the storage unit 510 to hold the position of the second rotating base portion 120 including the second clutch plate 132.

Subsequently, the electric joint portion 350 is manipulated, after which the clutch 130 is again engaged by letting the operator give an engagement command of the clutch 130 to the clutch drive signal input portion 520. At this time the clutch drive unit 530 is set such that whenever the manipulating rod 100 does not go back to the position status based on the angle θ stored in the storage unit 510, the clutch 130 is not engaged.

In such settings as described above, the operator issues a clutch 30 engagement command to the clutch drive signal input portion 520 to search for the position status based on the angle θ stored in the storage unit 510 while manipulating the manipulating rod 100.

As the manipulating rod 100 arrives at a position meeting the position status based on the angle θ, it causes the clutch drive portion 530 to engage the clutch 130.

It is thus possible to restore back the last motion status of the manual joint portion 370 upon re-engagement of the clutch 130, making it possible for the operator to implement more intuitive manipulations.

Yet another embodiment of the invention will now be explained with reference to FIG. 13 that is illustrative in schematic of the architecture of the manipulator 10 according thereto and FIG. 14 that is a block diagram of the manipulator 10 according thereto.

While the embodiment of the invention explained with reference to FIGS. 1 to 8 comprises only one electric joint portion 350, it is to be understood that the manipulator 10 according to the embodiment of the invention here includes a second electric joint portion 360 in addition to the electric joint portion 350.

The manipulator 10 according to the embodiment of the invention here includes third and fourth motors 213 and 214 for driving the second electric joint portion 360, which motors are corresponding to the first and second motors 211 and 212 for driving the electric joint portion 360.

While the architectures of the third and fourth motors 213 and 214 for driving the second electric joint portion 360 by way of a wire 257, etc. are not shown, it is to be noted that the architecture of the second electric joint portion 360, too, may be designed as is case with that of the electric joint portion 350.

The manipulator 10 according to the invention here also comprises a manipulating rod 100 having an electric joint selection switch 550 (electric joint portion selection switch) for selecting either the first electric joint portion 350 or the second electric joint portion 360 as the electric joint portion to be moved. An output from the electric joint selection switch 550 is entered in the main control unit 500. In response to the output from the electric joint selection switch 550, the main control unit 500 selects either driving of the first and second motors 211 and 212 to drive the first electric joint portion 350 or driving of the third and fourth motors 213 and 214 to drive the second electric joint portion 360.

While there are two electric joint portions provided in the embodiment of the invention here, it is to be understood that the number of electric joint portions used with the manipulator 10 is not limited to two.

According to such an embodiment as described above, the switching operation of the electric joint selection switch 550 provided on the manipulating rod 100 enables the single manipulating rod 100 to manipulate a plurality of electric joint portions.

A further embodiment of the invention will now explained. In much the same way as shown in FIGS. 13 and 14, the embodiment of the invention here, too, includes a plurality of electric joint portions, and what is schematically illustrated in FIG. 13 may be used for the general architecture of the manipulator 10 here.

On the other hand, what is illustrated in the block diagram of FIG. 15 may be used for control of the manipulator 10. This block diagram is different from the block diagram of FIG. 14 in that instead of the electric joint selection switch 550 there is an inverse kinetics analytical algorithm storage unit 570 provided.

A program stored in the inverse kinetics analytical algorithm storage unit 570 is referred to by the main control unit 500 at the time when it controls the first, second, third and fourth motors 211, 212, 213 and 214. A storage area in the microcomputer or, alternatively, a separate single memory may be used for the inverse kinetics analytical algorithm storage unit 570.

Pursuant to the program stored in the inverse kinetics analytical algorithm storage unit 570, the main control unit 500 solves inverse kinetics on the basis of the angle θ detected in response to manipulation of the manipulating rod 100 to determine the amount of controlling the first and second motors 211 and 212 that drive the first electric joint portion 350 and the amount of controlling the third and fourth motors 213 and 214 that drive the second electric joint portion 360.

While there are two electric joint portions provided in the embodiment of the invention here, it is to be understood that the number of electric joint portions used with the manipulator 10 is not limited to two.

According to such an embodiment as described above, it is possible to use only the manipulating rod 100 to facilitate manipulation of a plurality of electric joint portions.

It is to be noted that instead of providing a plurality of electric joint portions and using the electric joint selection switch 550 for selecting which of the electric joint portions is to be manipulated, it is possible to provide a plurality of manual joint portions and use the manual joint selection switch 560 as will be described later. In this case, there may be a plurality of clutches provided to transmit displacement of the manipulating rod 100 to the manual joint portions.

Although a clutch may be used as the manual joint selection switch 560 (manual joint portion selection switch) for selecting which of the manual joint portions is to be manipulated, an example of using a rack-and-pinion mechanism instead of the clutch will be explained hereinafter.

FIG. 16 is illustrative of an exemplary architecture of the manual joint selection switch 560 using such a rack-and-pinion mechanism. Note here that the manual joint selection switch 560 shown in FIG. 16 is capable of selecting either driving of the manual joint portion(s) or driving of the electric joint portion(s). FIG. 17 is a block diagram of a control system for the manipulator 10 when used in combination with the manual joint selection switch 560.

The manipulator 10 according to the embodiment of the invention here includes a first manual joint portion and a second manual joint portion, both not shown. A third wire 253 is fixed at one end to a first rack 410, and a fourth wire 254 is fixed at one end to a second rack 420. On the other hand, the third wire 253, and the fourth wire 254 is fixed at the other end to the first manual joint portion (not shown). The first manual joint portion moves with displacement of the third wire 253, and the fourth wire 254.

Likewise, a fifth wire 255 is fixed at one end to a third rack 430, and a sixth wire 256 is fixed at one end to a fourth rack 440. On the other hand, the fifth wire 255, and the sixth wire 256 is fixed at the other end to a second manual joint portion (not shown). The second manual joint portion moves with displacement of the fifth wire 255, and the sixth wire 256.

A first pinion 450 mates with both opposing first and second racks 410 and 420, and as the first pinion 450 rotates, it causes displacement of the third wire 253, and the fourth wire 254.

A second pinion 460 mate with both opposing third and fourth racks 430 and 430, and as the second pinion 460 rotates, it causes displacement of the fifth wire 255, and the sixth wire 256.

A manipulating rod 100 is provided with a manipulating rod pinion 400 having an axis of rotation overlapping with the center of rotation of the manipulating rod 100.

The manipulating rod 100 is capable of sliding for up-and-down movement in FIG. 16.

As the manipulating rod 100 slides toward a side (A), it causes the manipulating rod pinion 400 to be mating with the first rack 410.

As the manipulating rod 100 slides toward a side (B), it causes the manipulating rod pinion 400 to be in a state of mating with the fourth rack 440.

By such sliding movement of the manipulating rod 100, the manipulating rod 100 is allowed to select manipulation of either the first manual joint portion or the second manual joint portion.

When the manipulating rod 100 is at a position (C) shown in FIG. 16, a manipulating rod position detection unit 580 detects it to detect the amount of displacement of the manipulating rod 100 by the rotary encoder 150.

On the basis of the aforesaid amount of displacement, the main control unit 500 sends a control command signal to the first and second motors 211 and 212 that are devices for driving the electric joint portion 350 to control movement of the electric joint portion 350.

An exemplary manipulation of the manipulator 10 according to the embodiment of the invention as described above will now be explained with reference to FIGS. 18 to 20.

FIG. 18 shows that the manipulating rod 100 is sliding toward side (A) so that the manipulating rod pinion 400 is in a state of mating with the first rack 410 whereby the first manual joint portion is moving by the manipulating rod 100.

From this state the manipulating rod 100 slides into a state where the manipulating rod pinion 400 is not mating with any one of the first rack 410 or the fourth rack 440, as shown in FIG. 19. Here the electric joint portion 350 moves by manipulation of the manipulating rod 100.

FIG. 20 shows that the manipulating rod 100 is sliding toward Side (B) so that the manipulating rod pinion 400 is in a state of mating with the fourth rack 440 whereby the second manual joint portion is moving by the manipulating rod 100.

According to such an embodiment as described above, even a plurality of complicatedly assembled manual joint portions can be manipulated by the single manipulating rod 100, facilitating manipulations.

REFERENCE SIGNS LIST

10: manipulator
100: manipulating rod (manipulating part)
101: center of rotation
110: first rotating base portion
120: second rotating base portion
130: clutch (selection portion)
131: first clutch plate
132: second clutch plate
137: convex portion
138: concave portion
140: clutch status detection unit
150: rotary encoder (detection unit)
190: base case
211: first motor
212: second motor
213: third motor
214: fourth motor
231: first drive pulley
232: second drive pulley
233: third drive pulley
251: first wire
252: second wire
253: third wire
254: fourth wire
255: fifth wire
256: sixth wire
257: wire
271: first follower pulley
272: second follower pulley
310: first rigid tube
320: second rigid tube
350: (first) electric joint portion
353: joint ring
357: shaft member
360: (second) electric joint portion
363: joint ring
367: shaft member
370: manual joint portion
373: joint ring
375: distal-end joint ring
377: shaft member
400: manipulating rod pinion
410: first rack
420: second rack
430: third rack
440: fourth rack
450: first pinion
460: second pinion
500: main control unit
510: storage unit
520: clutch drive signal input portion
530: clutch drive portion
550: electric joint selection switch (electric joint portion selection switch)
560: manual joint selection switch (manual switch joint portion selection switch)
570: inverse kinetics analytical algorithm storage unit
580: manipulating rod position detection unit

The invention claimed is:

1. A manipulator, comprising:
a manipulating part,
a manual joint portion that is driven directly by displacement of the manipulating part,
a detection unit that detects an amount of displacement of the manipulating part,
a device that moves depending on the amount of displacement detected at the detection unit,
an electric joint portion that is driven by the device,
a selection portion that selectively determines whether the electric joint portion is driven or not, wherein the selection portion is a clutch, and
a disengagement position status holding portion configured to hold a position status between clutch plates upon disengagement of the clutch,
wherein the disengagement position status holding, portion comprises a convex portion provided on one clutch plate and a concave portion provided in another clutch plate.

2. The manipulator according to claim 1, wherein when driving of the manual joint portion is selected at the selection portion, the clutch is engaged to transmit the displacement of the manipulating part to the manual joint portion.

3. The manipulator according to claim 1, wherein when driving of the electric joint portion is selected at the selection portion, the clutch is disengaged to move the device depending on the amount of displacement detected at the detection unit.

4. The manipulator according to claim 1, which further comprises:
a plurality of the electric joint portions, and an electric joint portion selection switch for selecting which of the plurality of the electric joint portions is to be driven.

5. The manipulator according to claim 1, which further comprises:
a plurality of the electric joint portions,
a plurality of the devices corresponding to the plurality of the electric joint parts, respectively, and
a control unit for implementing operation based on the amount of displacement detected at the detection unit to issue commands to the plurality of the devices about how much each of the plurality of the devices is driven.

6. The manipulator according to claim 5, wherein the operation is an operation for solving inverse kinetics.

7. The manipulator according to claim 1, which further comprises:
a plurality of the manual joint portions, and a manual joint portion selection switch for selecting which of the plurality of the manual joint portions is to be driven.

* * * * *